United States Patent [19]

Holderbaum et al.

[11] Patent Number: 5,624,981

[45] Date of Patent: Apr. 29, 1997

[54] POLYALKYLPIPERIDINE CONTAINING ACETIC ACID AND 3-AMINO-ACRYLIC ACID DERIVATIVES

[75] Inventors: Martin Holderbaum, Ludwigshafen; Alexander Aumueller, Neustadt; Hubert Trauth, Dudenhofen, all of Germany

[73] Assignee: BASF Aktiengesellschaft, Ludwigshafen, Germany

[21] Appl. No.: 313,107

[22] PCT Filed: Mar. 26, 1993

[86] PCT No.: PCT/EP93/00739

§ 371 Date: Oct. 7, 1994

§ 102(e) Date: Oct. 7, 1994

[87] PCT Pub. No.: WO93/20051

PCT Pub. Date: Oct. 14, 1993

[30] Foreign Application Priority Data

Apr. 7, 1992 [DE] Germany ............... 42 11 603.1

[51] Int. Cl.[6] .................. C07D 211/68; C07D 211/08; C07D 401/00; C08K 5/34
[52] U.S. Cl. ................... 524/82; 524/83; 524/84; 524/95; 524/96; 524/97; 524/99; 524/100; 544/2; 544/66; 544/182; 544/192; 544/194; 544/212; 544/238; 544/335; 544/360; 546/138; 546/143; 546/162; 546/190; 546/192; 546/193; 546/195; 546/196; 546/197; 546/201
[58] Field of Search .................. 546/190, 193, 546/192, 138, 143, 162, 195, 196, 197, 201; 524/99, 100, 82, 83, 84, 95, 96, 97; 544/360, 192, 194, 212, 66, 335, 238, 2, 182

[56] References Cited

U.S. PATENT DOCUMENTS

| | | | |
|---|---|---|---|
| 3,079,366 | 2/1963 | Boyle et al. | 260/45.9 |
| 4,238,613 | 12/1980 | Rasberger et al. | 546/190 |
| 4,444,928 | 4/1984 | Karrer | 524/99 |
| 4,855,434 | 8/1989 | Cantatore et al. | 546/190 |

FOREIGN PATENT DOCUMENTS

| | | |
|---|---|---|
| 2654058 | 6/1977 | Germany. |
| WO93/20051 | 10/1993 | WIPO. |

*Primary Examiner*—C. Warren Ivy
*Assistant Examiner*—Raymond Covington
*Attorney, Agent, or Firm*—Oblon, Spivak, McClelland, Maier & Neustadt, P.C.

[57] ABSTRACT

Polyalkylpiperidine-containing acetic acid and 3-aminoacrylic acid derivatives I

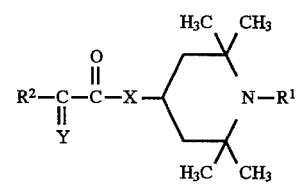

where $R^1$ is hydrogen, $C_1$- to $C_6$-alkyl, formyl, $C_2$- to $C_6$-alkanoyl, $C_1$- to $C_{12}$-alkoxy, $C_5$- to $C_6$-cycloalkoxy, cyanomethyl, hydroxymethyl, 2-hydroxyethyl or a radical of the formula —$CR^3$=CH—CO—$OR^4$, where $R^3$ is hydrogen, $C_1$-to $C_6$-alkyl or a radical of the formula —CO—$OR^4$ and $R^4$ is $C_1$- to $C_{20}$-alkyl, $C_5$- to $C_8$-cycloalkyl, $C_7$- to $C_{18}$-aralkyl, phenyl, tolyl or a radical of the formula —$(CH_2CH_2O)_n$H or —$[CH(CH_3)CH_2O]_n$H, where n is a number from 1 to 30, X is O, NH or $NR^6$, where $R^6$ is $C_1$- to $C_{12}$-alkyl, and Y is hydrogen or a group of the formula =CH—$NHR^7$ or =CH—$NR^6R^7$, where $R^7$ is phenyl which can be substituted by one to three $C_1$- to $C_{12}$-alkyl, $C_1$- to $C_{12}$-alkoxy, halogen, cyano, hydroxyl, phenyl or groups of the formula —CO—$OR^5$, —CO—$R^5$, —CO—$NHR^5$, —O—CO—$R^5$ or —NH—CO—$R^5$, is a 5- or 6-membered unsaturated or saturated heterocyclic ring having up to three hetero atoms from the group comprising nitrogen, oxygen and sulfur, which can additionally be benzo-fused and substituted by one to three $C_1$- to $C_{12}$-alkyl, $C_1$- to $C_{12}$-alkoxy, halogen, cyano, hydroxyl, phenyl, phenoxy or $C_1$- to $C_{12}$-alkoxycarbonyl are described.

11 Claims, No Drawings

POLYALKYLPIPERIDINE CONTAINING ACETIC ACID AND 3-AMINO-ACRYLIC ACID DERIVATIVES

This is the national stage application of PCT/EP 93/00739 filed Mar. 26, 1993.

The present invention relates to novel polyalkyl-piperidine-containing acetic acid and 3-aminoacrylic acid derivatives Ia

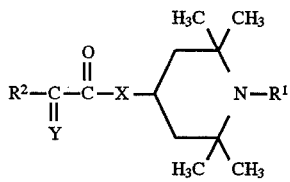

where $R^1$ is hydrogen, $C_1$- to $C_6$-alkyl, formyl, $C_2$- to $C_6$-alkanoyl, $C_1$- to $C_{12}$-alkoxy, $C_5$- to $C_6$-cycloalkoxy, cyanomethyl, hydroxymethyl, 2-hydroxyethyl, or a radical of the formula —$CR^3$=CH—CO—$OR^4$, where $R^3$ is hydrogen, $C_1$- to $C_5$-alkyl or a radical of the formula —CO—$OR^4$ and $R^4$ is $C_1$- to $C_{20}$-alkyl, $C_5$- to $C_8$-cycloalkyl, $C_7$- to $C_{18}$-aralkyl, phenyl, tolyl or a radical of the formula —$(CH_2CH_2O)_nH$ or —$[CH(CH_3)CH_2O]_nH$, where n is a number from 1 to 30, $R^2$ is cyano X is O, NH or $NR^6$ where $R^C_1$- is $C_{12}$-alkyl, and Y is hydrogen or a group of the formula =CH—$NHR^7$ or =NH—$NR^6R7$, where $R^7$ is phenyl which can be substituted by one to three $C_1$- to $C_{12}$-alkyl, $C_1$- to $C_{12}$-alkoxy, halogen, cyano, hydroxyl, phenyl or groups of the formula —CO—$OR^5$, —CO—$R^5$, —CO—$NHR^5$, —O—CO—$R^5$ or —NH—CO—$R^5$, where $R^5$ is $C_1$- to $C_{12}$-alkyl, $C_5$- to $C_8$-cycloalkyl, benzyl, phenyl or tolyl, is a 5- or 6-membered unsaturated or saturated heterocyclic ring having up to three hetero atoms from the group consisting of nitrogen, oxygen and sulfur, which can additionally be benzo-fused and substituted by one to three $C_1$- to $C_{12}$-alkyl, $C_1$- to $C_{12}$-alkoxy, halogen, cyano, hydroxyl, phenyl, phenoxy or $C_1$- to $C_{12}$-alkoxycarbonyl

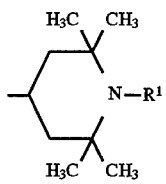

Furthermore, the invention relates to organic material stabilized against the action of light, oxygen and heat in particular stabilized plastics and coatings, which contains from 0.01 to 5% by weight, based on the amount of the organic material, of one or more polyalkylpiperidine containing acetic acid and 3-aminoacrylic acid derivatives of the general formula I

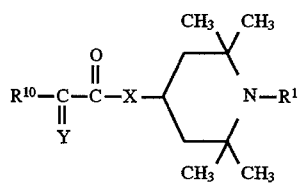

where $R^1$ is hydrogen, $C_1$- to $C_6$-alkyl, formyl, $C_2$- to $C_6$-alkanoyl, $C_1$- to $C_{12}$-alkoxy, $C_5$- to $C_6$-cycloalkoxy, cyanomethyl, hydroxymethyl, 2-hydroxyethyl or a radical of the formula —$CR^3$=CH—CO—$OR^4$ where $R^3$ is hydrogen, $C_1$- to $C_6$-alkyl or a radical of the formula —CO—$OR^4$ and $R^4$ is $C_1$- to $C_{20}$-alkyl, $C_5$- to $C_8$-cycloalkyl, $C_7$- to $C_{18}$-aralkyl, phenyl, tolyl or a radical of the formula —$(CH_2CH_2O)_nH$ or —$[CH(CH_3)CH_2O]_nH$, where n is a number from 1 to 30, $R^{10}$ is cyano, a radical of the formula —CO—$R^5$ or —CO—$OR^5$ or a group of the formula

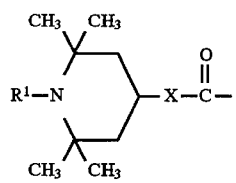

where $R^5$ is $C_1$- to $C_{12}$-alkyl, $C_5$- to $C_8$-cycloalkyl, benzyl, phenyl or tolyl, X is O, NH or $NR^6$, where $R^6$ is $C_1$- to $C_{12}$-alkyl, and Y is hydrogen or a group of the formula =CH-$NHR^7$ or =CH—$NHR^7$ or =CH—$NR^6R^7$, where $R^7$ is phenyl which can be substituted by one to three $C_1$- to $C_{12}$-alkyl, $C_1$-to $C_{12}$-alkoxy, halogen, cyano, hydroxyl, phenyl or groups of the formula —CO—$OR^5$, —CO—$R^5$, —CO—$NHR^5$, —O—CO—$R^5$ or —NH—CO—$R^5$, is a 5- or 6-membered unsaturated or saturated heterocyclic ring having up to three hetero atoms from the group consisting of nitrogen, oxygen and sulfur, which can additionally be benzo-fused and substituted by one to three $C_1$- to $C_{12}$-alkyl, $C_1$- to $C_{12}$-alkoxy, halogen, cyano, hydroxyl, phenyl, phenoxy or $C_1$- to $C_{12}$-alkoxycarbonyl.

As is known, organic material, in particular plastics and coatings, is destroyed very rapidly, in particular by the action of light. This destruction usually manifests itself as yellowing, discoloration, crack formation or embrittlement of the material. Satisfactory protection against the destruction of organic material by light, oxygen and heat should therefore be achieved using light stabilizers and stabilizers.

Thus, U.S. Pat. No. 3 079 366 (1) describes, inter alia, alkyl 3-(arylamino)-2-cyanoacrylates and alkyl 3-(aryl-amino)-2-(alkoxycarbonyl)acrylates as light stabilizers for plastics.

DE-A3 805 786 (2) relates to polyalkylpiperidinyl 3-(polyalkylpiperidinylamino)acrylates. These compounds are recommended as stabilizers for organic material, in particular synthetic polymers.

The unsatisfactory thing about compositions of the prior art of this type is often the compatibility with plastics, which is too low, the duration of the protective action, which is too small, the intrinsic color of the substances, the tendency for volatility and the thermal decomposition of the stabilizers during incorporation at elevated temperatures.

It is an object of the present invention to provide light stabilizers and/or stabilizers which provide more effective protection for organic material.

We have found that this object is achieved with the polyalkylpiperidine-containing acetic acid and 3-aminoacrylic acid derivatives I defined at the beginning.

Suitable straight-chain or branched alkyl for $R^1$, $R^3$ to $R^6$ and $R^8$, suitable substituents on the phenyl ring and on heterocyclic rings and a suitable alcohol in alkoxycarbonyl, which is referred to as $C_1$- to $C_4$-, $C_1$- to $C_6$-, $C_1$- to $C_{12}$- and $C_1$- to $C_{20}$-alkyl, are, for example, methyl, ethyl, n-propyl, isopropyl, n-butyl, isobutyl, sec-butyl, tert-butyl, n-amyl, isoamyl, sec-amyl, tert-amyl, neopentyl, n-hexyl, n-heptyl, n-octyl, 2-ethylhexyl, n-nonyl, isononyl, n-decyl, n-undecyl, n-dodecyl, n-tridecyl, isotridecyl, n-tetradecyl, n-pentadecyl, n-hexadecyl, n-heptadecyl, n-octadecyl and n-eicocyl. Preferred radicals are generally lower alkyl, especially $C_1$- to $C_4$-alkyl, in particular methyl and ethyl.

Suitable straight-chain or branched $C_2$- to $C_6$-alkanoyl for $R^1$ is in particular acetyl, but in addition also propionyl, butyryl, isobutyryl, pentanoyl and hexanoyl.

Suitable straight-chain or branched $C_1$- to $C_{12}$-alkoxy for $R^1$ and suitable substituents on the phenyl ring and on heterocyclic rings are especially $C_1$- to $C_4$-alkoxy such as methoxy, ethoxy, n-propoxy, isopropoxy, n-butoxy, isobutoxy, sec-butoxy and tert-butoxy, but in addition also n-pentoxy, n-hexoxy, isohexoxy, n-heptoxy, isoheptoxy, n-octoxy, 2-ethylhexoxy, isooctoxy, n-nonoxy, n-decoxy, n-undeocoxy and n-dodecoxy.

$C_5$- to $C_6$-cycloalkoxy for $R^1$ is especially cyclopentoxy and cyclohexoxy.

In the presence of a radical of the formula —$CR^3$=CH—CO—$OR^4$ for $R^1$, $R^3$ is preferably $C_1$- to $C_4$-alkoxycarbonyl such as, especially, methoxycarbonyl and ethoxycarbonyl or in particular hydrogen.

Suitable $C_5$- to $C_8$-cycloalkyl for $R^4$ and $R^5$ is especially $C_5$- to $C_6$-cycloalkyl, such as cyclopentyl and cyclohexyl, but in addition also cycloheptyl, cyclooctyl, methylcyclopentyl, dimethylcyclopentyl, methylcyclohexyl, ethylcyclohexyl and dimethylcyclohexyl.

Suitable $C_7$- to $C_{18}$-aralkyl for $R^4$ is, for example, naphthylmethyl, diphenylmethyl or methylbenzyl, but in particular $c_7$- to $C_{18}$-phenylalkyl such as 1-phenylethyl, 2-phenylethyl, 1-phenylpropyl, 2-phenylpropyl, 3-phenylpropyl, 2-phenylprop-2-yl, 4-phenylbutyl, 2,2-dimethyl-2-phenylethyl, 5-phenylamyl, 10-phenyldecyl, 12-phenyldodecyl or especially benzyl.

Suitable tolyl is ortho-, meta- and especially p-tolyl.

The degree of alkoxylation n in polyoxyethylene and polyoxypropylene for $R^4$ is preferably from 1 to 10, in particular from 2 to 7, very particularly preferably from 3to5.

Halogen atoms are understood as meaning fluorine and iodine, but especially bromine and in particular chlorine.

Suitable 5- or 6-membered unsaturated or saturated heterocyclic rings having up to 3 hetero atoms from the group consisting of nitrogen, oxygen and sulfur, which can additionally be benzo-fused and substituted by the radicals signified, are:

Tetrahydrofuran, furan, tetrahydrothiophene, thiophene, pyrrolidine, pyrroline, pyrrole, isoxazole, oxazole, thiazole, pyrazole, imidazoline, imidazole, 1,2,3-triazolidine, 1,2,3- and 1,2,4 -triazole, 1,2,3-, 1,2,4- and 1,2,5-oxadiazole, tetrahydropyran, dihydropyran, 2H- and 4H-pyran, piperidine, 1,3- and 1,4-dioxane, morpholine, pyrazan, pyridine, pyrimidine, pyridazine, pyrazine, 1,2,5-oxathiazine, 1,3,5-, 1,2,3 and 1,2,4-triazine, benzofuran, thionaphthene, indoline, indole, isoindoline, benzoxazole, indazole, benzimidazole, chroman, isochroman, 2H-and 4H-chromene, quinoline, isoquinoline, 1,2,3,4 -tetrahydroisoquinoline, cinnoline, quinazoline, quinoxalene, phthalazine and benzo-1,2,3-triazine.

If substituted phenyl radicals occur as radicals $R^7$ and $R^9$, the preferred degree of substitution is 2, or in particular 1. Singly substituted phenyl radicals are ortho-, meta- or preferably para-substituted, doubly substituted phenyl radicals often have a 2,4-substitution pattern and triply substituted phenyl radicals often have a 2,4,6-substitution pattern. When two or three substituents occur these can be identical or different.

The stuctures I and Ia in the case in which Y is a group of the formula =CH—$NHR^7$ or =CH—$NR^6R^7$ includes, with reference to the spatial position of the substituents on the C=C double bond in the compounds I, both the respective E- and Z-isomers. Of course, mixtures of both isomers can also occur.

A preferred embodiment are compounds I and Ia where $R^1$ is hydrogen, methyl, formyl, acetyl, cyanomethyl, hydroxymethyl or a radical of the formula —CH=CH—CO—$OR^8$, where $R^8$ is $C_1$- to $C_4$-alkyl, $C_5$- to $C_6$-cycloalkyl, benzyl, phenyl, tolyl or a radical of the formula —$(CH_2CH_2O)_m$ or —$[CH(CH_3)CH_2O]_mH$, where m is a number from 1 to 10.

A further preferred embodiment are compounds I where $R^{10}$ is cyano or $C_1$- to $C_4$-alkoxycarbonyl.

A further preferred embodiment are compounds I and Ia where Y is hydrogen or a group of the formula =CH—$NHR^9$, where $R^9$ is phenyl which can be substituted by one or two $C_1$- to $C_4$-alkyl, $C_1$- to $C_4$-alkoxy, chlorine, cyano, hydroxyl or $C_1$- to $C_4$-alkoxycarbonyl, or is a 6-membered unsaturated or saturated heterocyclic ring having up to three nitrogen atoms which can additionally be benzofused and substituted by one or two $C_1$- to $C_4$-alkyl, $C_1$- to $C_4$-alkoxy, chlorine, cyano, hydroxyl or $C_1$- to $C_4$-alkoxycarbonyl.

Suitable heterocyclic rings for $R^9$ are particularly pyridine, pyrimidine, pyridazine, pyrazine and 1,3,5-triazine.

The polyalkylpiperidine-containing acetic acid and 3-aminoacrylic acid derivatives I can be prepared by methods known per se.

Compounds I where Y is a group of the formula =CH—$NHR^7$ or =CH—$NR^6R^7$ can be prepared, for example, by reacting alkyl cyanoacetates, alkyl malonates or alkyl acetoacetates, the methyl or ethyl esters being particularly suitable in this connection, trialkyl orthoformate and aromatic or heterocyclic amines of the formula $R^7$-$NH^2$ or $R^7$-$NHR^6$.

Triethyl orthoformate or trimethyl orthoformate is particularly preferred here.

The reaction is expediently carried out in a suitable polar organic solvent such as an alcohol, for example n-propanol, n-butanol, ethylene glycol, diethylens glycol, ethylene glycol monomethyl ether or cyclohexanol. Suitable solvents are also carboxamides such as dimethylformamide or excess trialkyl orthoformate. If the starting compounds used already form a liquid mixture, an additional solvent can be dispensed with.

In the case of very long reaction times, the catalysts which can be used for the reaction are, if desired, additionally Lewis acids such as boric acid, $AlCl_3$, $ZrCl_4$, $TiCl_4$ or especially $ZnCl_2$ in the amounts customary for this purpose.

The alkyl 3-aminoacrylates thus prepared can be converted into the corresponding polyalkylpiperidine-containing derivatives I without problems. This is expediently carried out by transesterifying with, for example, 2,2,6,6-tetramethyl-4-piperidinol in an inert organic solvent such as toluene or xylene in the presence of a catalyst such as tetrabutyl orthotitanate, phenothiazine, lithium amide or dibutyltin acetate.

Polyalkylpiperidinyl-substituted amides of the formula I or Ia are formed in an advantageous manner by reacting the alkyl cyanoacetates, alkyl malonates or alkyl acetoacetates mentioned above with triacetonediamine and, if desired, subsequently reacting with aromatic or heterocyclic amines of the formula $R^7$-$NH_2$ or $R^7$-$NHR^6$ as described above.

If in the compounds I and Ia the radical $R^1$ is an acrylic acid ester group, compounds I in which $R^1$ is hydrogen are expediently reacted with acetylenecarboxylic acid derivatives such as propionic acid esters or acetylenedicarboxylic acid esters to prepare those compounds.

The compounds I or Ia according to the invention are outstandingly suitable for stabilizing organic material against the action of light, oxygen and heat. They are also active as metal deactivators. They are added to the organic material to be stabilized in a concentration of from 0.01 to 5% by weight, preferably of from 0.02 to 2% by weight, based on the organic material, before, during or after its preparation.

Organic material is understood as meaning, for example, cosmetic preparations such as ointments and lotions, pharmaceutical formulations such as pills and suppositories, photographic recording materials, in particular photographic emulsions, or precursors for plastics and coatings, but in particular plastics and coatings themselves.

The present invention additionally relates to organic material stabilized against the action of light, oxygen and heat, in particular plastics and coatings, which contains the compounds I or Ia in the abovementioned concentrations.

To mix the compounds I or Ia, with plastics, all known apparatus and methods for the blending of stabilizers or other additives in polymers can be used.

The organic material stabilized by the compounds I or Ia according to the invention may possibly contain further additives, for example antioxidants, light stabilizers, metal deactivators, antistats, flame retardants, pigments and fillers.

Antioxidants and light stabilizers which can be added in addition to the compounds I or Ia are, for example, compounds based on sterically hindered phenols or sulfur- or phosphorus-containing costabilizers.

Phenolic antioxidants of this type which may be mentioned are, for example, 2,6-di-tert-butyl-4-methyl-phenol, n-octadecyl β-(3,5-di-tert-butyl-4-hydroxyphenyl propionate, 1,1,3-tris(2-methyl-4-hydroxy-5-tert-butylphenyl) butane, 1,3,5-trimethyl-2,4,6-tris (3,5-di -tert-butyl-4-hydroxybenzyl) benzene, 1,3,5-tris (3,5-di -tert-butyl-4-hydroxybenzyl) isocyanurate, 1,3,5-tris[β-3,5-di-tert-butyl-4-hydroxyphenyl) propionylethyl] isocyanurate, 1,3,5-tris(2,6-dimethyl-3-hydroxy-4-tert-butylbenzyl) isocyanurate and pentaerythritol tetrakis[β-(3,5-di-tert-butyl-4-hydroxyphenyl)propionate].

Suitable phosphorus-containing antioxidants are, for example, tris(nonylphenyl) phosphite, distearylpentaerythritol diphosphite, tris(2,4-di-tert-butylphenyl) phosphite, tris (2-tert-butyl-4-methylphenyl) phosphite, bis(2,4-di-tert-butylphenyl)pentaerythritol diphosphite and tetrakis(2,4-di-tert-butylphenyl)-4,4'-biphenylene diphosphite.

Examples of sulfur-containing antioxidants which may be mentioned are dilauryl thiodipropionate, dimyristyl thiodipropionate, distearyl thiodipropionate, pentaerythritol tetrakis(β-laurylthiopropionate) and pentaerythritol tetrakis (β-hexylthiopropionate).

Other antioxidants and light stabilizers which can be used together with the compounds I or Ia are, for example, 2-(2'-hydroxyphenyl)benzotriazole, 2-hydroxybenzophenone, aryl estes of hydroxybenzoic acids, α-cyanocinnamic derivatives, benzimidazolecarboxanilides, nickel compounds or oxalic acid dianilides.

A particularly good stabilization is obtained when at least one other light stabilizer from the sterically hindered amine compound class is additionally added to the compounds I or Ia in a customary concentration.

Other suitable sterically hindered amines for this purpose are, for example: bis(2,2,6,6-tetramethylpiperidyl) sebacate, bis(1,2,2,6,6-pentamethylpiperidyl) sebacate, the condensation product of 1-hydroxyethyl -2,2,6,6-tetramethyl-4-hydroxypiperidine and succinic acid, the condensation product of N,N'-(2,2,6,6-tetramethylpiperidyl) hexamethylenediamine and 4-tert-octyl -amino-2,6-dichloro-1,3,5-triazine, tris(2,2,6,6-tetramethylpiperidyl) nitrilotriacetate, tetrakis(2,2,6,6-tetramethyl-4-piperidyl)-1, 2,3,4-butanetetracarboxylic acid, 1,1'-(1,2-ethanediyl)-bis (3,3,5,5-tetramethylpiperazinone), the condensation products of 4-amino -2,2,6,6-tetramethylpiperidines and tetramethylolacetylenediureas.

Examples of plastics which may be mentioned which can be stabilized by the compounds I or Ia are:

Polymers of mono- and diolefins, such as, for example, low or high density polyethylene, polypropylene, linear poly-1-butene, polyisoprene, polybutadiene and copolymers of monoolefins or diolefins or mixtures of the said polymers;

copolymers of monoolefins or diolefins with other vinyl monomers, such as, for example, ethylene-alkyl acrylate copolymers, ethylene-alkyl methacrylate copolymers, ethylene-vinyl acetate copolymers or ethyleneacrylic acid copolymers;

polystyrene and copolymers of styrene or α-methylstyrene with dienes and/or acrylic derivatives, such as, for example, styrene-butadiene, styrene-acrylonitrile (SAN), styrene-ethyl methacrylate, styrene-butadiene-ethyl acrylate, styrene-acrylonitrile-methacrylate, acrylonitrile-butadiene-styrene (ABS) or methyl methacrylate-butadiene-styrene (MBS);

halogen-containing polymers, such as, for example, polyvinyl chloride, polyvinyl fluoride, polyvinylidene fluoride and their copolymers;

polymers which are derived from α,β-unsaturated acids and their derivatives, such as polyacrylates, polymethacrylates, polyacrylamides and polyacrylonitriles;

polymers which are derived from unsaturated alcohols and amines or from their acrylic derivatives or acetals, for example polyvinyl alcohol and polyvinyl acetate;

polyurethanes, polyamides, polyureas, polyesters, polycarbonates, polysulfones, polyether sulfones and polyether ketones.

Furthermore, coats, for example industrial finishes, can be stabilized using the compounds I or Ia. Among these, baked finishes, among these in turn automotive finishes, preferably 2-coat finishes, are particularly to be emphasized.

The compounds I or Ia according to the invention can be added to the coating in solid or dissolved form. Their good solubility in coating systems is particularly advantageous here.

Preferably, the compounds I or Ia according to the invention are used for stabilizing polyurethanes, polyesters, polystyrene, polyolefins such as ethylene or propylene polymers, polyamides and also ABS and SAN polymers, in particular molding materials, and coats, in particular from acid-curing coatings.

Another preferred field of use is the stabilization of polypropylene and polyamide fibers.

The compounds I or Ia are distinguished by a good compatibility with the customary types of plastics and by a good solubility and an excellent compatibility in the customary coating systems. As a rule, they have no, or only a very slight, intrinsic color, are stable and non-volatile at the customary plastics and coating processing temperatures and especially effect a long period of protection of the materials treated with them.

The examples illustrate the invention. The preparation conditions were not optimized.

PREPARATION EXAMPLES

EXAMPLE 1

35.5 g (0.16 mol) of N-(2,2,6,6-tetramethylpiperidin-4-yl)cyanoacetamide were heated to 110° C. with 44.4 g (0.3 mol) of triethyl orthoformate and 18.8 g (0.2 mol) of aniline. Over a period of from 3 to 5 h, ethanol was slowly removed by distillation, the temperature rising to about 125° C. The mixture was then cooled and the product obtained was recrystallized from isopropanol using active carbon. 38 g (corresponding to a yield of 73%) of N-(2',2',6',6'-tetramethylpiperidin-4'-yl)-3-(phenylamino)-2-cyanoacrylamide were obtained in the form of colorless crystals of melting point 162° C.

The spectroscopic data are given in Table 1.

EXAMPLES 2 TO 12

In a similar manner to Example 1, the products listed in Table 1 were prepared from N-(2,2,6,6-tetramethylpiperidin-4-yl)cyanoacetamide using the corresponding aromatic or heterocyclic amines. The melting points and the spectroscopic data of the products are also given in Table 1.

TABLE 1

Structure, melting point and spectroscopic data of the products of Examples 1 to 12 having the general formula

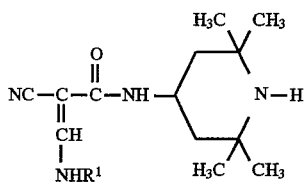

| Ex. No. | R⁷ | Melting point [°C.] | UV Data (CH₃OH) λ$_{max}$ [nm] | ε |
|---|---|---|---|---|
| 1 | Phenyl | 162 | 319 | 28 100 |
| 2 | 4-Methoxyphenyl | 200 (EA) | 329 | 36 300 |
| 3 | 4-Methylphenyl | 184–86 (EA) | 324 | 29 700 |
| 4 | 2,4-Dimethoxyphenyl | 155 | 345 | 28 000 |
| 5 | 3,5-Dimethylphenyl | 160 (EA) | 322 | 27 900 |
| 6 | 2-Methoxy-4-ethoxycarbonylphenyl | 163 | 335 | 45 900 |
| 7 | 2-Methoxycarbonyl-phenyl | 168–70 | 337 | 31 000 |
| 8 | 4-Chlorophenyl | 186 | 325 | 33 700 |
| 9 | 4-Cyanophenyl | 213–15 | 333 | 48 100 |
| 10 | 2-Pyridinyl | 167 | 326 | 39 300 |
| 11 | 4-Hydroxyphenyl | 245 | 330 | 22 400 |
| 12 | 2-Pyrimidinyl | 152 | 313 | 35 500 |

(EA) means that the product was recrystallised from ethylacetate with the addition of active carbon.

EXAMPLE 13

22.3 g (0.1 mol) of N-(2,2,6,6-tetramethylpiperidin-4-yl) cyanoacetamide were refluxed for 3 hours with 10.3 g (0.105 mol) of ethyl propiolate in 100 ml of ethanol. After cooling, the precipitate formed was filtered off and recrystallized from ethanol. 26 g (corresponding to a yield of 80%) of the product of the formula

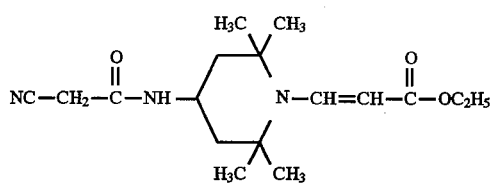

were obtained in the form of colorless crystals of melting point from 189° to 190° C.

UV data (CH₃OH): λ$_{max}$=282 nm, ε=30,400

EXAMPLE 14a 32.6 g (0.1 mol) of the compound from Example 1 were refluxed for 10 hours with 9.8 g (0.1 mol) of ethyl propiolate in 50 ml of ethanol. After cooling, the precipitate formed was filtered off and recrystallized from ethanol. 30 g (corresponding to a yield of 70 %) of 3-aminoacrylamide were obtained in the form of colorless crystals of melting point 194°–95° C.

The spectroscopic data are given in Table 2.

EXAMPLE 14b 32.1 g (0.1 mol) of the compound from Example 13, 30 g (0.2 mol) of triethyl orthoformate and 9.3 g (0.1 mol) of aniline were heated at from 110° to 120° C. for 5 h, 13 ml of ethanol distilling off. The mixture was then cooled, and the precipitate formed was filtered off and recrystallized from ethanol with the addition of active carbon. 12 g (corresponding to a yield of 28%) of the same compound as in Example 14a were obtained.

EXAMPLES 15 TO 23

In a similar manner to Example 14a, the products shown in Table 2 were prepared from the compounds of Examples 2, 3, 5, 6, 7, 9, 10, 11, and 12 and ethyl propiolate. The melting points and the spectroscopic data of the products are also given in Table 2.

TABLE 2

Structure, melting point and spectroscopic data of the products of Examples 13 to 23 having the general formula

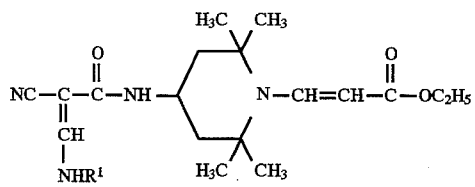

| Ex. No. | $R^7$ | Melting point [°C.] | UV Data ($CH_3OH$) $\lambda_{max}$ [nm] | $\epsilon$ |
|---|---|---|---|---|
| 14a | Phenyl | 194–95 | 286 | 38 800 |
|  |  |  | 320 | 37 000 |
| 15 | 4-Methoxyphenyl | 175 | 287 | 35 500 |
|  |  |  | 329 | 28 200 |
| 16 | 4-Methylphenyl | 206–08 | 286 | 36 500 |
|  |  |  | 324 | 34 000 |
| 17 | 3,5-Dimethylphenyl | 180 | 285 | 34 000 |
|  |  |  | 324 | 33 800 |
| 18 | 2-Methoxy-4-ethoxycarbonylphenyl | 218–19 | 284 | 31 800 |
|  |  |  | 335 | 53 000 |
| 19 | 2-Methoxycarbonyl-phenyl | 176 | 285 | 30 200 |
|  |  |  | 337 | 33 000 |
| 20 | 4-Cyanophenyl | 221–23 | 285 | 28 800 |
|  |  |  | 339 | 47 700 |
| 21 | 2-Pyridinyl | 206–08 | 279 | 38 400 |
|  |  |  | 325 | 34 800 |
| 22 | 4-Hydroxyphenyl | 210 | 287 | 37 600 |
|  |  |  | 330 | 28 600 |
| 23 | 2-Pyrimidinyl | 199 | 286 | 50 000 |
|  |  |  | 312 | 46 600 |

EXAMPLE 24

44.8 g (0.2 mol) of 2,2,6,6-tetramethyl-4-piperidinyl cyanoacetate were heated at 110° C. for from 3 to 4 h with 18.6 g (0.2 mol) of aniline and 59.2 g (0.4 mol) of triethyl orthoformate, ethanol distilling off and the temperature rising to 130° C. After the majority of the ethanol had been distilled off, the mixture was cooled. The residue obtained was stirred with 100 ml of acetone, and the product was filtered off and washed with diethyl ether. 43 g (corresponding to a yield of 66%) of 2',2', 6',6'-tetramethyl-4'-piperidinyl 3-(phenylamino)-2-cyanoacrylate were obtained in the form of colorless crystals of melting point from 113° to 117° C.

The spectroscopic data are given in Table 3.

EXAMPLES 25 to 30

In a similar manner to Example 24, the products shown in Table 3 were prepared from 2,2,6,6-tetramethyl-4-piperidinyl cyanoacetate using the corresponding aromatic or heterocyclic amines. The melting points and the spectroscopic data of the products are also given in Table 3.

TABLE 3

Structure, melting point and spectroscopic data of the products of Examples 25 to 30 having the general formula

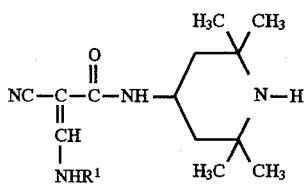

| Ex. No. | $R^7$ | Melting point [°C.] | UV Data ($CH_3OH$) $\lambda_{max}$ [nm] | $\epsilon$ |
|---|---|---|---|---|
| 24 | Phenyl | 113–17 | 319 | 27 200 |
| 25 | 4-Methoxyphenyl | 131–34 | 328 | 25 500 |
| 26 | 4-Methylphenyl | 156 | 323 | 23 800 |
| 27 | 4-Ethoxycarbonylphenyl | 192–95 | 332 | 42 000 |
| 28 | 3,5-Dimethylphenyl | 144 | 322 | 28 600 |
| 29 | 4-Hydroxyphenyl | 135–39 | 329 | 20 300 |
| 30 | 15-Methylpyridin-2-yl | 164 | 329 | 33 300 |

EXAMPLES 31 to 35

In a similar manner to Example 14a, the products shown in Table 4 were prepared from the compounds of Examples 24, 25, 26, 27 or 28 and ethyl propiolate. The melting points and the spectroscopic data of the products are also given in Table 4.

TABLE 4

Structure, melting point and spectroscopic data of the products of Examples 31 to 35 having the general formula

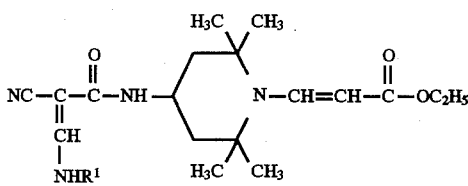

| Ex. No. | $R^7$ | Melting point [°C.] | UV Data ($CH_3OH$) $\lambda_{max}$ [nm] | $\epsilon$ |
|---|---|---|---|---|
| 31 | Phenyl | 172 | 284 | 28 000 |
|  |  |  | 333 | 23 700 |
| 32 | 4-Methoxyphenyl | 192–95 | 287 | 34 400 |
|  |  |  | 322 | 30 400 |
| 33 | 4-Methylphenyl | 165 | 286 | 38 000 |
|  |  |  | 218 | 34 300 |
| 34 | 4-Ethoxycarbonyl-phenyl | 157 | 292 | 17 800 |
|  |  |  | 333 | 47 300 |
| 35 | 3,5-Dimethylphenyl | 179 | 285 | 32 700 |
|  |  |  | 322 | 31 100 |

We claim:

1. A polyalkylpiperidine-containing acetic acid or 3-aminoacrylic acid derivative of the general formula Ia

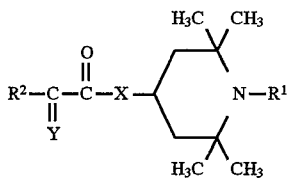

Ia where

R[1] is hydrogen, $C_1$- to $C_6$-alkyl, formyl, $C_2$- to $C_6$-alkanoyl, $C_1$- to $C_{12}$-alkoxy, $C_5$- to $C_6$-cycloalkoxy, cyanomethyl, hydroxymethyl, 2-hydroxyethyl or a radical of the formula —$CR^3$=CH—CO—$OR^4$, where R[3] is hydrogen, $C_1$- to $C_6$- alkyl or a radical of the formula —CO—$OR^4$ and R[4] is $C_1$- to $C_{20}$-alkyl, $C_5$- to $C_8$-cycloalkyl, $C_7$- to $C_{18}$-aralkyl, phenyl, tolyl or a radical of the formula —$(CH_2CH_2O)_n$H or —$[CH(CH_3)CH_2O]_n$H, where n is a number from 1 to 30, R[2] is cyano, X is O, NH or $NR^6$, where R[6] is $C_1$- to $C_{12}$-alkyl, and Y is a group of the formula =CH—$NHR^7$ or =CH—$NR^6R^7$, where R[7] is phenyl which can be substituted by one to three $C_1$- to $C_{12}$-alkyl, $C_1$- to $C_{12}$-alkoxy, halogen, cyano, hydroxyl, phenyl or groups of the formula —CO—$OR^5$, —CO—$R^5$, —CO—$NHR^5$, —O—CO—$R^5$ or —NH—CO—$R^5$, where $R^5$ is $C_1$- to $C_{12}$-alkyl, $C_5$- to $C_8$-cycloalkyl, benzyl, phenyl or tolyl, is a 5- or 6-membered unsaturated heterocyclic ring having up to three hetero atoms from the group consisting of nitrogen, oxygen and sulfur, which can additionally be benzo-fused and substituted by one to three $C_1$- to $C_{12}$-alkyl, $C_1$- to $C_{12}$-alkoxy, halogen, cyano, hydroxyl, phenyl, phenoxy or $C_1$- to $C_{12}$-alkoxycarbonyl.

2. A polyalkylpiperidine-containing acetic acid or 3-aminoacrylic acid derivative Ia as claimed in claim 1, where R[1] is hydrogen, methyl, formyl, acetyl, cyanomethyl, hydroxymethyl or a radical of the formula —CH=CH—CO—$OR^8$, where $R^8$ is $C_1$- to $C_4$-alkyl, $C_5$- to $C_6$-cycloalkyl, benzyl, phenyl, tolyl or a radical of the formula —$(CH_2CH_2O)_m$ or —$[CH(CH_3)CH_2O]_m$H, where m is a number from 1 to 10.

3. A polyalkylpiperidine-containing acetic acid or 3-aminoacrylic acid derivative Ia as claimed in claim 1, where Y is a group of the formula =CH—$NHR^9$, where $R^9$ is phenyl which can be substituted by one or two $C_1$- to $C_4$-alkyl, $C_1$- to $C_4$-alkoxy, chlorine, cyano, hydroxyl or $C_1$- to $C_4$-alkoxycarbonyl, or is a 6-membered unsaturated heterocyclic ring having up to three nitrogen atoms, which can additionally be benzo-fused and substituted by one or two $C_1$- to $C_4$-alkyl, $C_1$- to $C_4$-alkoxy, chlorine, cyano, hydroxyl or $C_1$- to $C_4$-alkoxycarbonyl.

4. An organic material stabilized against the action of light, oxygen and heat, containing from 0.01 to 5% by weight, based on the amount of the organic material, of one or more polyalkylpiperidine containing acetic acid and 3-aminoacrylic acid derivatives of the general formula I

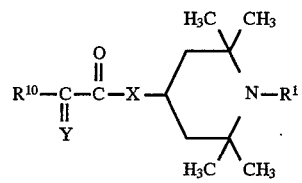

I where

R[1] is hydrogen, $C_1$- to $C_6$- alkyl, formyl, $C_2$- to $C_6$-alkanoyl, $C_1$- to $C_{12}$-alkoxy, $C_5$- to $C_6$-cycloalkoxy, cyanomethyl, hydroxymethyl, 2 -hydroxyethyl or a radical of the formula —$CR^3$=CH—CO—$OR^4$, where R[3] is hydrogen, $C_1$- to $C_6$-alkyl or a radical of the formula —CO—$OR^4$ and R[4] is $C_1$- to $C_{20}$-alkyl, $C_5$- to $C_8$-cycloalkyl, $C_7$- to $C_{18}$-aralkyl, phenyl, tolyl or a radical of the formula —$(CH_2CH_2O)_n$H or —$[CH(CH_3)CH_2O]_n$H, where n is a number from 1 to 30, R[10] is cyano, a radical of the formula —CO—$R^5$ or —CO—$OR^5$ or a group of the formula

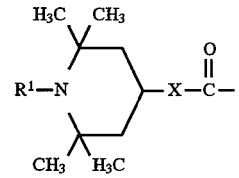

where

R[5] is $C_1$- to $C_{12}$-alkyl, $C_5$- to $C_8$-cycloalkyl, benzyl, phenyl or tolyl, X is O, NH or $NR^6$ where R[6] is $C_1$- to $C_{12}$-alkyl, and Y is a group of the formula =CH—$NHR^7$ or =CH—$R^6R^7$, where R[7] is phenyl which can be substituted by one to three $C_1$- to $C_{12}$-alkyl, $C_1$- to $C_{12}$-alkoxy, halogen, cyano, hydroxyl, phenyl or groups of the formula —CO—$OR^5$, —CO—$R^5$, —CO—$NHR^5$, —O—CO—$R^5$ or —NH—CO—$R^5$, is a 5- or 6-membered unsaturated heterocyclic ring having up to three hetero atoms from the group consisting of nitrogen, oxygen and sulfur, which can additionally be benzo-fused and substituted by one to three $C_1$- to $C_{12}$-alkyl, $C_1$- to C12-alkoxy, halogen, cyano, hydroxyl, phenyl, phenoxy or $C_1$- to $C_{12}$-alkoxycarbonyl.

5. A plastic or coating stabilized against the action of light, oxygen and heat, containing from 0.01 to 5% by weight, based on the amount of the plastic or coating, of one or more compounds I as claimed in claim 4.

6. A method for stabilizing organic material against the action of light, oxygen and heat, which comprises using a compound I as claimed in claim 4 for this purpose.

7. A method for stabilizing plastics and coatings against the action of light, oxygen and heat, which comprises using a compound I as claimed in claim 4 for this purpose.

8. A polyalkylpiperidine-containing acetic acid or 3-aminoacrylic acid derivative Ia as claimed in claim 1, wherein R[7] is a substituted or unsubstituted five-membered or six-membered unsaturated heterocyclic ring having at least one double bond.

9. A polyalkylpiperidine-containing acetic acid or 3-aminoacrylic acid derivative Ia according to claim 8, wherein $R^7$ is selected from the group consisting of furan, thiophene, pyrroline, pyrrole, isoxazole, oxazole, thiazole, pyrazole, imidazoline, imidazole, 1,2,3- and 1,2,4-triazole, 1,2,3-, 1,2,4- and 1,2,5-oxadiazole, dihydropyran, 2H- and 4H-pyran, pyridine, pyrimidine, pyridazine, pyrazine, 1,2,5-oxathiazine, 1,3,5-, 1,2,3- and 1,2,4-triazine, benzofuran, thionaphthene, indole, benzoxazole, indazole, benzimidazole, 2H- and 4H- chromene, quinoline, isoquinoline, cinnoline, quinazoline, quinoxalene, phthalazine and benzo-1,2,3-triazine.

10. A polyalkylpiperidine-containing acetic acid or 3-aminoacrylic acid derivative Ia according to claim 1, wherein $R^7$ is an unsubstituted or substituted heteroaromatic ring.

11. A polyalkylpiperidine-containing acetic acid or 3-aminoacrylic acid derivative Ia according to claim 10, wherein $R^7$ is selected from the group consisting of furan, thiophene, pyrrole, isoxazole, oxazole, thiazole, pyrazole, imidazole, 1,2,3- and 1,2,4-triazole, 1,2,3-, 1,2,4- and 1,2,5-oxadiazole, pyridine, pyrimidine, pyridazine, pyrazine, 1,3,5-, 1,2,3- and 1,2,4-triazine, benzofuran, thionaphthene, indole, benzoxazole, indazole, benzimidazole, quinoline, isoquinoline, cinnoline, quinazoline, quinoxalene, phthalazine and benzo-1,2,3-triazine.

\* \* \* \* \*